(12) United States Patent
Wiemer et al.

(10) Patent No.: US 8,508,728 B2
(45) Date of Patent: Aug. 13, 2013

(54) EMPTY BOTTLE INSPECTION

(75) Inventors: Heinrich Wiemer, Hamburg (DE); Horst Böcker, Schwerte (DE)

(73) Assignee: KHS GmbH, Dortmund (DE)

( * ) Notice: Subject to any disclaimer, the term of this patent is extended or adjusted under 35 U.S.C. 154(b) by 276 days.

(21) Appl. No.: 12/996,741

(22) PCT Filed: Jul. 9, 2009

(86) PCT No.: PCT/EP2009/004974
§ 371 (c)(1),
(2), (4) Date: Dec. 7, 2010

(87) PCT Pub. No.: WO2010/017863
PCT Pub. Date: Feb. 18, 2010

(65) Prior Publication Data
US 2011/0102783 A1    May 5, 2011

(30) Foreign Application Priority Data
Aug. 14, 2008 (DE) .......................... 10 2008 037 727

(51) Int. Cl.
*G01N 21/00* (2006.01)

(52) U.S. Cl.
USPC ........................................................ 356/239.4

(58) Field of Classification Search
None
See application file for complete search history.

(56) References Cited

U.S. PATENT DOCUMENTS

| | | | |
|---|---|---|---|
| 3,684,385 | A | 8/1972 | Einfalt |
| 4,213,042 | A | 7/1980 | Beach et al. |
| 4,367,405 | A | 1/1983 | Ford |
| 5,020,908 | A | 6/1991 | Hermann |
| 5,486,692 | A | 1/1996 | Baldwin |

FOREIGN PATENT DOCUMENTS

| | | |
|---|---|---|
| DE | 2940122 | 4/1980 |
| DE | 3815539 | 11/1989 |
| EP | 0222959 | 5/1987 |
| EP | 1 724 569 | 11/2006 |
| FR | 2 882 148 | 8/2006 |
| JP | 57 007546 | 1/1982 |
| JP | 11 201906 | 7/1999 |
| WO | 2005/071391 | 8/2005 |
| WO | 2006/011803 | 2/2006 |

OTHER PUBLICATIONS

Database WPI Week 200443, Mar. 2, 2004, Thomson Scientific, London, GB; AN 2004-459125, XP002545463.

*Primary Examiner* — Gregory J Toatley
*Assistant Examiner* — Amanda Merlino
(74) *Attorney, Agent, or Firm* — Occhiuti Rohlicek & Tsao LLP

(57) ABSTRACT

The invention relates to an inspection apparatus (1) for inspection of bottles (2) or similar containers, comprising at least one lighting device (9, 11) and one camera (12, 13) which form an inspection bridge (6). The inspection bridge (6) has on the inspection side (7) thereof a first lighting device (9) and a first camera (12), wherein at an inspection side (8) of the inspection bridge (6) located opposite the first inspection side (7), there is a second lighting device (11) and a second camera (13).

11 Claims, 2 Drawing Sheets

EMPTY BOTTLE INSPECTION

CROSS-REFERENCE TO RELATED APPLICATIONS

Figure 1:
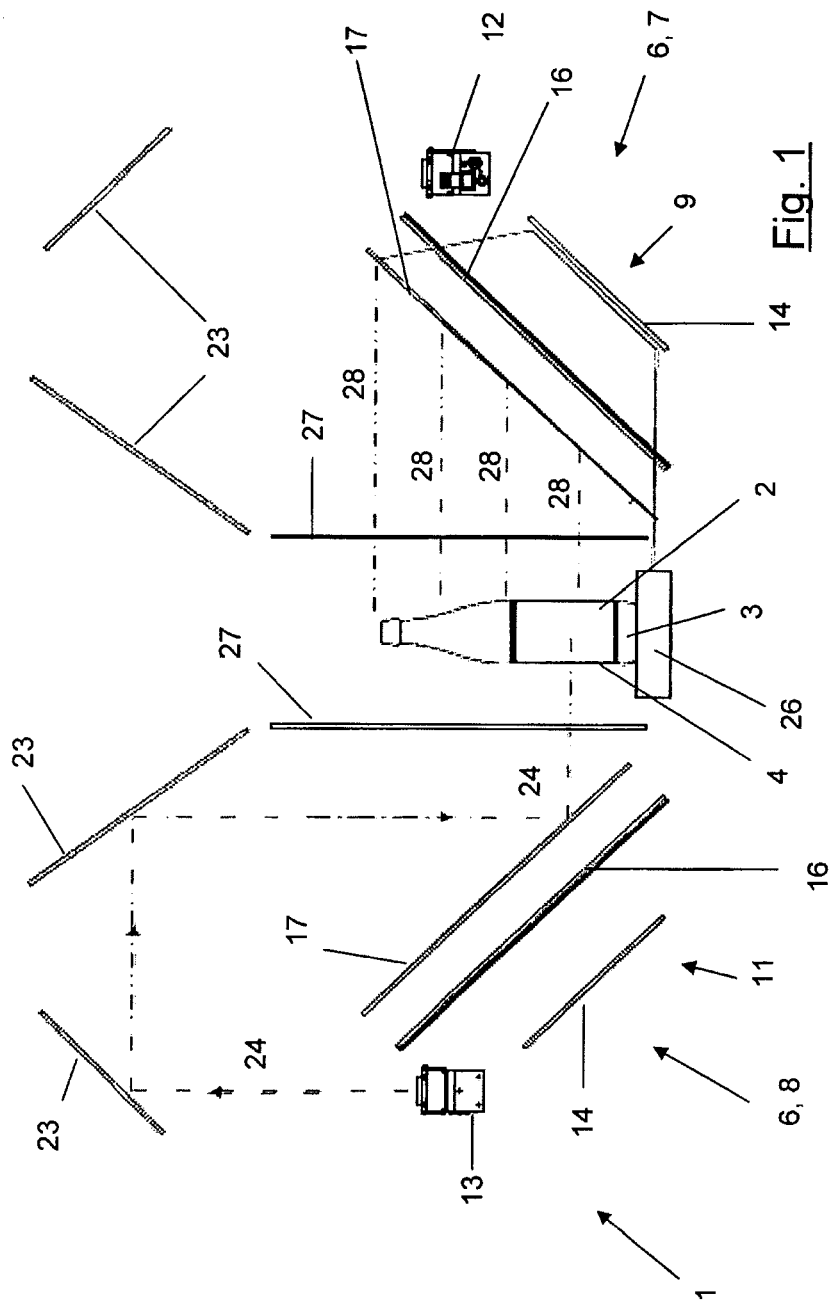

This application is the National Stage of International Application No. PCT/EP2009/004974, filed on Jul. 9, 2009, which claims the benefit of German Application Serial No. 10 2008 037 727.9 filed on Aug. 14, 2008. The contents of both of the foregoing applications are hereby incorporated by reference in their entirety.

The invention relates to an inspection device for checking bottles or similar containers, said inspection device comprising at least one illuminating device and one camera, which form a first inspection bridge.

These types of bottles or similar containers can be used for liquids, for example for beverages. The containers can be produced from a transparent or translucent material, for example glass, or from a translucent plastics material, e.g. PET. Preferably once they have been cleaned, the bottles or similar containers are moved past the inspection device on a conveyor in the empty state. To this end, an illuminating device is located, for example, in relation to the bottle in question such that it shines through said bottle, the at least one first camera being located opposite thereto. The illuminating device shines through the bottle in question such that the at least first camera can check whether, for example, there are any foreign bodies, such as, for example, adhesive films, packing film (cellophane) or other unwanted objects, contaminants or whether there is damage in or on the bottle. The illuminating device with the camera located opposite can also be identified as an inspection bridge. However, only a certain region of the bottle in question is checked by means of this first inspection bridge (illuminating device/camera). In order to be able to obtain an overall image of the bottle question, inspection bridges are consequently provided one after the other when viewed in the direction of transport of the bottle in question. On the path of the respective bottles to each of the following inspection bridges, the bottles in question are rotated on in each case by 45° in order to obtain a photograph of another region in each case when the bottle in question passes the so-called inspection bridge. Four so-called inspection bridges following one after the other are therefore necessary in order to carry out a full inspection of the bottle in question. This means, however, in a disadvantageous manner, that the inspection device, when viewed in the direction of transport, has to extend over a long length in order to carry out a full inspection of the bottle in question, as at least four so-called consecutive inspection bridges are necessary.

Consequently, it is the object of the invention to improve an inspection device of the aforementioned type using simple means such that the previously mentioned disadvantages for a complete inspection of the containers or of the bottle in question can be avoided.

The object is achieved according to the invention by an inspection device with the features of Claim 1, wherein the inspection bridge has a first illuminating device and a first camera at its first inspection side, wherein a second illuminating device and a second camera are located at an inspection bridge that is located opposite the first inspection side.

An inspection bridge in terms of the invention is a device, which, with reference to a conveyor, has two oppositely situated inspection sides, wherein a container or a bottle to be inspected is moved along a direction of transport, preferably centrally between the oppositely situated sides past said inspection bridges.

In a preferred development, the first illuminating device has a light source, a first optical component and a beam splitter.

The first optical component is located, with reference to the light source, between said light source and the beam splitter. In an expedient manner, the first optical component has a lens, preferably a Fresnel lens, a polarisation filter and diffuser material. The polarisation filter is realized in a preferred development as polarisation film.

In a favourable manner, the lens, in its preferred development as a Fresnel lens, is provided quasi as the first optical layer of the first optical component with reference to the light source. The polarisation filter and the diffuser material are provided as quasi second optical layer of the first optical component, which is located, with reference to the light source, behind the first optical layer.

In a preferred development the light source is realized as an LED lamp.

The beam splitter is advantageously realized such that said beam splitter allows through light emitted from the light source, operating on the other hand, however, quasi as a mirror. This means that the beam splitter allows through the light emitted by the corresponding light source, wherein light falling on the side of the beam splitter situated opposite the corresponding light source is reflected. The side of the beam splitter situated opposite the corresponding light source can consequently also be identified as the mirror side.

The second illuminating device that is located opposite the first illuminating device on the inspection bridge is preferably realized in an identical manner to the first illuminating device.

In addition, the inspection bridge has optical mirrors that correlate with the first camera, said mirrors being aligned such that the first camera is aligned with the mirror side of the beam splitter of the first illuminating device, and can record an image of a container. Obviously the inspection bridge on the side situated opposite thereto also has optical mirrors that correlate with the second camera.

In this respect a first inspection bridge is formed, which, with reference to a central axis or with reference to the conveyor, is realized in each case in an identical manner on its oppositely situated sides or on its oppositely situated inspection sides, A container, for example a bottle, can be inspected using the transillumination method by way of the first inspection bridge over half of its circumference.

The bottle in question is supplied to the inspection device or to the first inspection bridge on a conveyor. The light source of the first illuminating device, in this case, emits a pulsating flash-like light beam, which shines through the bottle in question. The image of the transilluminated bottle is reflected at the beam splitter (mirror side) of the second illuminating device such that the second camera can take a corresponding image by means of the optical rerouting of the optical mirror provided. Naturally the second illuminating device does not emit any light whilst the first illuminating device transmits the flash-like LED light beam.

Once the first image has been taken, the bottle in question is conveyed further in the direction of transport. Normally speaking, the conveyor is realized quasi as an ascending conveyor, a plurality of bottles being located one behind another on the conveyor when viewed in the direction of transport. The individual bottles are spaced apart somewhat when viewed in the direction of transport, such that a gap is formed between directly following containers. The invention harnesses this circumstance in that shortly (e.g. 100 µs) after the transillumination of the bottle by means of the first illuminating device, the second illuminating device is activated, sends out a flash of light, and the bottle is transilluminated in this way from the other side with reference to the first illuminating device. The image of the transilluminated bottle is reflected at the beam splitter of the first illuminating device such that a corresponding image can be taken by the first camera. The advantage here is that the first camera is aligned such that said camera quasi follows the bottle moving on the conveyor in the direction of transport such that an image of the bottle rotated quasi by 45°, for example, relative to the first image is taken, without the bottle in this case having had to be rotated on the transporter by the corresponding amount. In this respect, on account of the development of the inspection device according to the invention, a simplified conveyor can be used which could be realized without any rotating devices. Half the circumference of the bottle in question can be inspected in this way by means of the first inspection bridge.

In order to inspect the region of the bottle not yet inspected, it is provided in an expedient manner that a second inspection bridge follows the first inspection bridge in the direction of transport of the bottle in question. The second inspection bridge is realized favourably in an identical manner to the first inspection bridge, that is with a third and fourth illuminating device and camera and optical mirrors correlating thereto, and enables an inspection of the regions of the bottle in question not yet inspected.

In this respect an improved inspection device is made available which enables a full inspection of the bottle in question by way of only two inspection bridges. The inspection device according to the invention can consequently be realized with a shorter longitudinal extension in comparison to the prior art when viewed in the direction of transport of the bottle in question, on account of the fact that two of the four inspection bridges that have been needed up to now can be omitted. This means that a considerable amount of space is saved. In addition, it is advantageous in terms of the invention for the bottle in question no longer to have to be rotated about its vertical axis. In this respect when designing the conveyor, there is no longer any need for rotating devices.

The inspection device according to the invention, with its compact design, is suitable preferably for empty bottle inspection. By means of the inspection device according to the invention, empty bottles can be inspected using the transillumination method, for example for unwanted foreign bodies located in their interior, for contaminants or for damage, to name, in a non restrictive manner, but a few examples for inspection.

Figure 2:
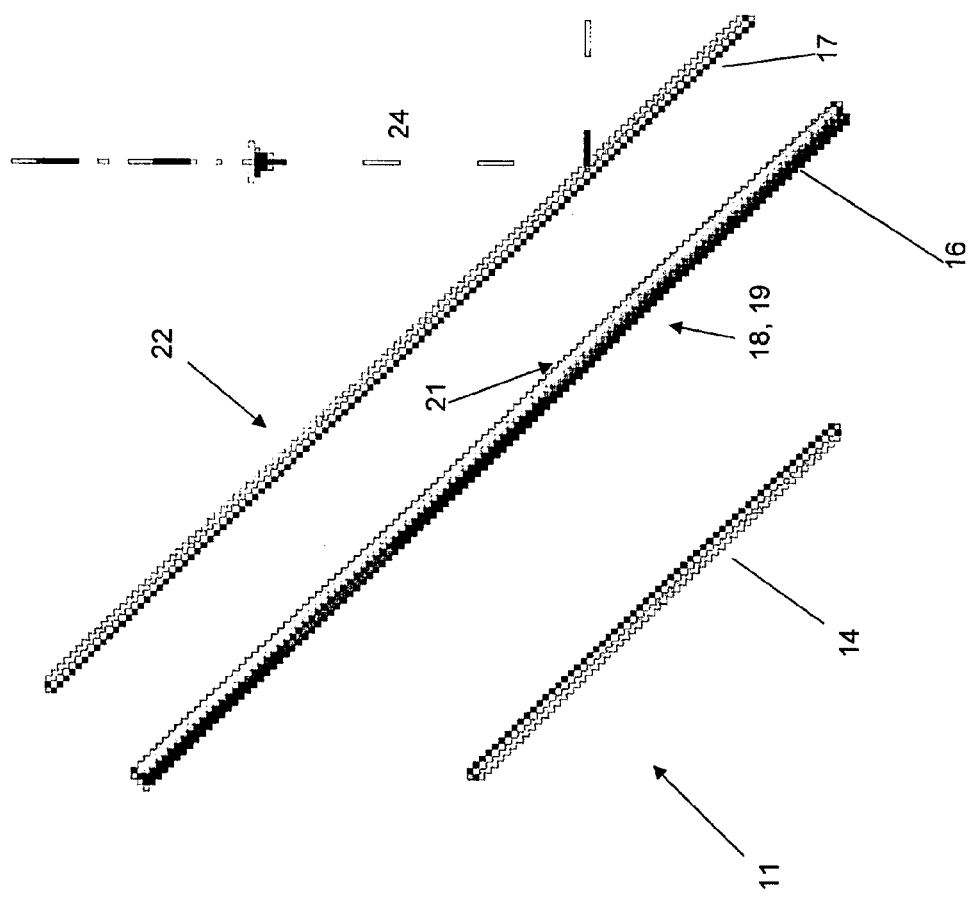

Further advantageous developments of the invention are disclosed in the sub claims and in the following description of the Figures, in which:

FIG. 1 shows an inspection device according to the invention with one single inspection bridge, the inspection sides of which are realized in an identical manner and FIG. 2 shows an enlarged representation of an illuminating device.

Identical parts in the various Figures are always provided with the same references, which is why, as a rule, they are only described once.

FIG. 1 shows an inspection device 1 for checking bottles 2 or similar containers. Bottles 2 or similar containers are identified below in general as bottle 2. The bottle 2 can be produced from a transparent or translucent material, for example glass, or from a translucent plastics material, e.g. PET.

The bottle 2 has a bottom 3 and a side wall 4. A mouth opening is located opposite the bottom 2. Using the inspection device 1, preferably the interior of the bottle 2, preferably after it has been cleaned, can be checked for unwanted objects, contaminants and/or damage. In this respect, it can also be termed an empty bottle inspection.

The inspection device 1 has a first inspection bridge 6, which has an illuminating device 9, 11 and a camera 12, 13 on each of its respective inspection sides 7 and 8. A second inspection bridge, when seen in the direction of transport of the bottle 2, is located behind the first inspection bridge 6 and is not shown. The illuminating device 9 located on the right in the drawing plane, that is on the inspection side 7, can also be identified as first illuminating device 9 and the camera 12 located on the same side can be identified as first camera 12. Analogous to this, the illuminating device 11 located on the left in the drawing plane, that is on the inspection side 8, is also identified as second illuminating device 11 and the camera 13 located at that location is identified as second camera 13.

The first illuminating device 9 is realized in an identical manner to the second illuminating device 11, which is why only the first illuminating device 9 is described below.

The first illuminating device 9 has a light source 14, a first optical component 16 and a beam splitter 17. The first optical component 16 is located between the light source 16 and the beam splitter 17. The spacing between the respective components is provided simply as an example and is not true to scale.

The light source 14 is realized as a LED light source.

The first optical component 16 (FIG. 2) has as first optical layer 18 a lens 19, preferably a Fresnel lens, and as second optical layer 21 a polarisation filter and diffuser material. The first optical layer 18 is located on the light source side, the second optical layer 21 is located on the beam splitter side. The polarisation filter is realized as polarisation film, the diffuser material in a preferred embodiment being known under the identification LSD® Light Shaping Diffuser. LSD®60°, LSD®40° and/or LSD®30° Angle, Acrylic-UVT or Glass-BK7 are preferably conceivable as diffuser material.

The beam splitter 17 of the first illuminating device 9 is realized such that said beam splitter allows through light emitted from the light source 14 of the first illuminating device 9, operating on the other side, however, as a mirror. This means that the beam splitter 17 allows through the light emitted by the corresponding light source 14, light falling on the side of the beam splitter 17 situated opposite the corresponding light source being reflected. This side can consequently also be identified as mirror side 22 (FIG. 2). An enlarged representation of the second illuminating device 11 is shown in FIG. 2.

The first camera 12 has associated therewith optical mirrors 23 that correlate on the inspection side 7 such that the first camera 12 is aligned in the direction of the mirror side 22. This is shown in principle by a beam arrow 24, the camera 12 being naturally realized with a zoom lens, which means that not only the point represented by means of the principle beam arrow 24, but the entire mirror side 22 can be taken by the first camera 12.

As represented, the inspection side 8 is realized in an identical manner to the inspection side 7.

The bottle 2 in question stands upright by way of its bottom 3 on a conveyor 26, and is moved in a direction of transport between the inspection sides 7 and 8 past the first inspection bridge 6. A second optical component 27, which has a polarisation filter and diffuser material, is located in each case between the two illuminating devices 9 and 11 and the bottle 2 in question.

The light source 14 of the first illuminating device 9 on the inspection side 7 flashes on. The light emitted passes the first optical component 16 and the beam splitter 17 and passes through the second optical component 27 to the bottle, transilluminating said bottle. This is represented by means of the beam arrow 28.

The image of the transilluminated bottle is reflected on the mirror side 22 of the beam splitter 17 of the inspection side 8 and is taken by the second camera 13 of the inspection side 8. The camera 13 is naturally connected to corresponding image processing devices.

A plurality of bottles are arranged one after the other on the conveyor 26 when seen in the direction of transport, spaced apart a little such that a gap is formed between directly consecutive bottles 2. Naturally, the bottle 2 is conveyed on further in the direction of transport when the afore-described first photograph is taken. Once the light source 14 of the inspection side 7 is deactivated, the light source 14 of the inspection side 8 is activated, such that said inspection side emits flashes of quasi pulsating light. The two light sources 14 emit flashes of quasi pulsating light. For example, the light source 14 of the inspection side 8 is activated about 100 μs after the deactivation of the light source 14 of the inspection side 7, with the time specified being in no way restrictive.

The light emitted from the light source 14 of the inspection side 8 passes the first optical component 16 of the inspection side 8, the beam splitter 17 of the inspection side 8, the second optical component 27 of the inspection side 8 and shines through the bottle 2. The image of the transilluminated bottle 2 is reflected on the mirror side 22 of the beam splitter 17 of the inspection side 7, and passes via the direction change of the optical mirror 23 correlating with the first camera 12 into the camera 12. In an expedient manner, the optical path of the camera 12 is set such that said camera looks quasi into the gap behind the bottle 2, such that an image of another bottle region, with reference to the first image, is taken. The optical path, in this case, is adjustable such that an image rotated by 45° with reference to the first image is taken without having to locate devices for rotating the bottles on the conveyor. The camera 12 is obviously also connected to image processing devices.

Consequently, half the circumference of the bottle in question 2 is already inspected by way of the first inspection bridge 6. The regions of the bottle 2 in question not yet inspected can be inspected by the following inspection bridge (not shown).

Each inspection bridge has a respective illuminating device and a respective camera on each inspection side 7 or 8. Thus, in an advantageous manner, where there are two inspection bridges following one after the other, four illuminating devices and four cameras are located on the inspection device. These are, however, advantageously located on just two inspection bridges. For inspecting the bottle in question, said bottle does not have to be rotated when passing the inspection device. Rather, by using the inspection device according to the invention, there is no need for special rotating devices on the conveyor.

In the exemplary embodiment represented in FIG. 1, the respective illuminating device 9 or 11 with its components 14, 16 and 17 are located at a 45° angle with reference to the bottle 2. Said angular amount is naturally only to be understood as an example. In the embodiment represented, the angle is selected such that the bottle 2 is reflected entirely on the mirror side 22 of the beam splitter 17.

The respective illuminating device can obviously be accommodated with its components.

LIST OF REFERENCES

1 Inspection device
2 Bottle
3 Bottom
4 Side wall of 2
5
6 Inspection bridge
7 Inspection side of 6
8 Inspection side of 6
9 Illuminating device
10
11 Illuminating device
12 Camera
13 Camera
14 Light source
15
16 First optical component
17 Beam splitter
18 First optical layer
19 Lens
20
21 Second optical layer
22 Mirror side of 17
23 Optical mirror
24 Beam arrow
25
26 Conveyor
27 Second optical component
28 Beam arrow

The invention claimed is:

1. An apparatus comprising an inspection device for checking bottles, said inspection device comprising at least a first illuminating device and a second illuminating device, and at least a first camera and a second camera, said at least a first illuminating device and a second illuminating device and said at least a first camera and a second camera forming an inspection bridge, wherein said inspection bridge comprises, on a first inspection side thereof, said first illuminating device, and said first camera, and on a second inspection side opposite the first inspection side, said second illuminating device and said second camera, wherein said second illuminating device has a structure identical to said first illuminating device, wherein said first and second illuminating devices each comprise a light source, a beam splitter, and a first optical component between said light source and said beam splitter, wherein said first illuminating device and said second illuminating device each have a first optical component, said first optical component including a first optical layer and a second optical layer, wherein said first optical layer comprises a lens, and wherein said second optical layer comprises a polarization filter and a diffuser material, wherein said beam splitters each comprise a mirror side and an opposite side and are arranged so that light from said light source of said respective illuminating device of said first inspection side is directed towards a bottle to be inspected, said bottle being trans-illuminated, and wherein light from said trans-illuminated bottle is reflected on said mirror side of said beam splitter of said second inspection side to said second camera, whereby said second camera captures said light whereby, in operation, said light source of said illuminating device of said first inspection side emits a flash of light that traverses said first optical component and said beam splitter and passes through said second optical component, thereby trans-illuminating said bottle, said second camera captures an image of said trans-illuminated bottle, said image having been reflected from said mirror side of said beam splitter of said second inspection side, and after deactivation of said light source of said illuminating device of said first inspection side, said light source of said illuminating device of said second inspection side emits a flash of light that traverses said second optical component and said beam splitter and passes through said first optical component, thereby trans-illuminating said bottle, and said first camera captures an image of said trans-illuminated bottle, said image having been reflected from said mirror side of said beam splitter of said first inspection side.

2. The apparatus of claim 1, wherein the first camera and the second camera each have, associated therewith, correlating optical mirrors.

3. The apparatus of claim 1, further comprising a second inspection bridge realized in an identical manner to the first inspection bridge, wherein when viewed in the direction of transport, the second inspection bridge follows the first inspection bridge.

4. The apparatus of claim 3, wherein an optical path of said second inspection bridge is set such that an image rotated 45 degrees relative to an image from said first inspection bridge is captured, said bottle being aligned un-rotated.

5. The apparatus of claim 1, wherein said first optical layer comprises a Fresnel lens and said second optical layer comprises a polarization filter and a diffusing material, wherein said first optical layer is arranged on a side facing said light source and said second optical layer is arranged on a side facing one of said beam splitters.

6. The apparatus of claim 5, wherein said polarization filter comprises a polarizing film.

7. The apparatus of claim 6, wherein said diffusing material is selected from the group consisting of acrylic UVT and BK7 glass.

8. The apparatus of claim 1, wherein at least one of said light sources comprises an LED light source.

9. The apparatus of claim 1, further comprising a second optical component comprising a polarizing filter and a diffusing material, said second optical component being arranged between one of said beam splitters and a space through which a bottle to be inspected is guided.

10. A method of inspecting bottles on a conveyor using an inspection device comprising at least a first and second illuminating device, at least a first and second camera, said at least a first and second illuminating device and said at least a first and second camera forming an inspection bridge, wherein said inspection bridge comprises, on a first inspection side thereof, said first illuminating device, and said first camera, and on a second inspection side opposite the first inspection side, said second illuminating device and said second camera, wherein said second illuminating device is realized in an identical manner to said first illuminating device, wherein said first and second illuminating devices each comprise a light source, a beam splitter, and a first optical component between said light source and said beam splitter, wherein said first illuminating device and said second illuminating device each have a first optical component, said first optical component including a first optical layer and a second optical layer, wherein said first optical layer comprises a lens, and wherein said second optical layer comprises a polarization filter and a diffuser material, wherein said beam splitters each comprise a mirror side and an opposite side and are arranged so that light from said light source of said respective illuminating device of said first inspection side is directed towards a bottle to be inspected, said bottle being trans-illuminated, and wherein light from said trans-illuminated bottle is reflected on said mirror side of said beam splitter of said second inspection side to said second camera, whereby said second camera captures said light, said method comprising causing said light source of said illuminating device of said first inspection side to emit a flash of light, said light traversing said first optical component and said beam splitter and passing through said second optical component, thereby trans-illuminating said bottle, using said second camera, capturing an image of said trans-illuminated bottle, said image having been reflected from said mirror side of said beam splitter of said second inspection side, and after deactivation of said light source of said illuminating device of said first inspection side, causing said light source of said illuminating device of said second inspection side to emit a flash of light, said light traversing said second optical component and said beam splitter and passing through said first optical component, thereby trans-illuminating said bottle, and using said first camera, capturing an image of said trans-illuminated bottle, said image having been reflected from said mirror side of said beam splitter of said first inspection side.

11. The method of claim 10, further comprising waiting at least 100 microseconds after deactivation of said light source before causing said light source of said illuminating device of said second inspection side to emit said flash of light, and wherein said first and second light sources emit alternate.

\* \* \* \* \*